(12) United States Patent
Rees et al.

(10) Patent No.: US 11,020,551 B2
(45) Date of Patent: Jun. 1, 2021

(54) SYSTEM AND A CORRESPONDING METHOD FOR ESTIMATING RESPIRATORY DRIVE OF MECHANICALLY VENTILATED PATIENTS

(71) Applicant: Mermaid Care A/S, Nørresundby (DK)

(72) Inventors: Stephen Edward Rees, Gistrup (DK); Dan Stieper Karbing, Aalborg (DK); Sebastian Larraza Rico, Aalborg (DK)

(73) Assignee: Mermaid Care A/S, Nørresundby (DK)

( * ) Notice: Subject to any disclaimer, the term of this patent is extended or adjusted under 35 U.S.C. 154(b) by 855 days.

(21) Appl. No.: 14/893,446

(22) PCT Filed: May 22, 2014

(86) PCT No.: PCT/DK2014/050143
§ 371 (c)(1),
(2) Date: Nov. 23, 2015

(87) PCT Pub. No.: WO2014/187465
PCT Pub. Date: Nov. 27, 2014

(65) Prior Publication Data
US 2016/0121064 A1 May 5, 2016

(30) Foreign Application Priority Data

May 24, 2013 (DK) .......................... PA 2013 70283
Mar. 12, 2014 (DK) .......................... PA 2014 70120

(51) Int. Cl.
*A61M 16/00* (2006.01)
*A61M 16/12* (2006.01)

(52) U.S. Cl.
CPC .... *A61M 16/0069* (2014.02); *A61M 16/0003* (2014.02); *A61M 16/026* (2017.08);
(Continued)

(58) Field of Classification Search
CPC .............. A61M 16/00; A61M 16/0003; A61M 2016/003; A61M 2016/0042;
(Continued)

(56) References Cited

U.S. PATENT DOCUMENTS

| 4,867,152 A * | 9/1989 | Kou ...................... A61M 16/00 128/204.21 |
| 4,917,080 A * | 4/1990 | Bayerlein ............. A61M 16/00 128/204.23 |

(Continued)

FOREIGN PATENT DOCUMENTS

CN 102215750 A 10/2011

OTHER PUBLICATIONS

Rees, Stephan, Dan Karbing, Charlotte Allerod, Marianne Toftegaard, Per Thorgaard, Egon Toft, Soren Kjaergaard, Steen Andreassen. "The Intelligent Ventilator Project: Application of Physiological Models in Decision Support." AIME 2011, LNAI 6747, pp. 149-158.*

(Continued)

*Primary Examiner* — Quang D Thanh
*Assistant Examiner* — Jacqueline M Pinderski
(74) *Attorney, Agent, or Firm* — Dinsmore & Shohl LLP

(57) ABSTRACT

The present invention relates to a system (10) and a corresponding method for estimating the respiratory drive (R_DRIVE) of mechanically ventilated patients, and for preferably apportioning this respiratory drive into one, or more, components related to the chemical drive—i.e. the drive due to the chemoreceptor response—and/or the muscular drive—i.e. the contraction of respiratory muscles, for example the diaphragm. The principle of the invention is that respiratory drive can be obtained from measuring the patient's response to small changes in mechanical ventilation settings (Vt_SET), and that this can be apportioned into (Continued)

chemical and/or muscular effects depending upon the changes in respiratory frequency, and/or arterial or end tidal $CO_2$ levels, and/or arterial blood p H.

20 Claims, 8 Drawing Sheets

(52) U.S. Cl.
CPC ..... *A61M 16/12* (2013.01); *A61M 2016/0027* (2013.01); *A61M 2016/0039* (2013.01); *A61M 2016/0042* (2013.01); *A61M 2202/0464* (2013.01); *A61M 2205/3334* (2013.01); *A61M 2230/202* (2013.01); *A61M 2230/205* (2013.01); *A61M 2230/208* (2013.01); *A61M 2230/42* (2013.01); *A61M 2230/432* (2013.01); *A61M 2230/435* (2013.01)

(58) Field of Classification Search
CPC .......... A61M 16/0021; A61M 16/0022; A61M 16/0024; A61M 16/0026; A61M 16/0027; A61M 2016/0413; A61M 16/0841; A61M 16/085; A61M 16/0858; A61M 16/0069; A61M 16/12; A61M 2016/10; A61M 2016/1005; A61M 2016/102; A61M 2016/1025; A61M 2016/103; A61M 2016/0039; A61M 2202/0464; A61M 2205/0464; A61M 2205/3334; A61M 2230/202; A61M 2230/205; A61M 2230/208; A61M 2230/42; A61M 2230/432; A61M 2230/435
See application file for complete search history.

(56) References Cited

U.S. PATENT DOCUMENTS

| | | | |
|---|---|---|---|
| 8,122,885 B2 * | 2/2012 | Berthon-Jones | A61M 16/024 128/204.18 |
| 2003/0010339 A1 * | 1/2003 | Banner | A61M 16/026 128/204.18 |
| 2005/0098178 A1 | 5/2005 | Banner et al. | |
| 2008/0295839 A1 | 12/2008 | Habashi | |
| 2010/0228142 A1 * | 9/2010 | Sinderby | A61B 5/08 600/533 |
| 2010/0258123 A1 * | 10/2010 | Somaiya | A61M 16/024 128/204.23 |
| 2011/0263998 A1 * | 10/2011 | Heyer | A61B 5/08 600/529 |
| 2012/0272961 A1 * | 11/2012 | Masic | A61M 16/0051 128/204.23 |

OTHER PUBLICATIONS

Jubran, Amal. "Pulse Oximetry." Critical Care, 1999, vol. 3, No. 2.*
Medical Dictionary, "Chemoreceptor—definition of a chemoreceptor", Nov. 6, 2012. (Year: 2012).*
Lin, Shyan-Lung, Nai-Ren Guo, and Chuang-Chien Chiu. "Modeling and Simulation of Respiratory Control with LabVIEW". 2010. Journal of Medical and Biological Engineering, 32(1): 51-60. (Year: 2010).*
Gotzsche, Mette, Stinne Klitgaard Nielsen, and Stephen Rees. "A combined model of respiratory drive and acid-base status". 2009. Proceedings of the 7th IFAC Symposium on Modelling and Control in Biomedical Systems, Aalborg, Denmark. (Year: 2009).*
Huang, C. C., Y. H. Tsai, M. C. Lin, C. T. Yang, M. J. Hsieh, and R. S. Lan. "Respiratory Drive and Pulmonary Mechanics During Haemodialysis with Ultrafiltration in Ventilated Patients". 1997. Anaesthesia and Intensive Care, vol. 25, No. 5. (Year: 1997).*
Rees S. E. et al.: "The Intelligent Ventilator Project: Application of Physiological Models in Decision Support", Jul. 2, 2011, ECCV 2016 Conference; from book [Lecture Notes in Computer Science]; Springer International Publishing Cham, pp. 149-158.
Karbing D. S. et al.: "Retrospective evaluation of a decision support system for controlled mechanical ventilation", Med Biol Eng Comput, Springer, Berlin, DE, vol. 50, No. 1, Nov. 22, 2011, pp. 43-51.
International Search Report dated Jul. 21, 2014 for International Application No. PCT/DK2014/050143 filed May 22, 2014, 7 pages.
Rees et al.; "Using physiological models and decision theory for selecting appropriate ventilator settings," Journal of Clinical Monitoring and Computing, vol. 20, No. 6, pp. 421-429, Sep. 2006.

* cited by examiner

SYSTEM AND A CORRESPONDING METHOD FOR ESTIMATING RESPIRATORY DRIVE OF MECHANICALLY VENTILATED PATIENTS

CROSS REFERENCE TO RELATED APPLICATIONS

This application is a U.S. National Phase Application of PCT International Application Number PCT/DK2014/050143, filed on May 22, 2014, designating the United States of America and published in the English language, which is an International Application of and claims the benefit of priority to Danish Patent Application No. PA 2013 70283, filed on May 24, 2013, and Danish Patent Application No. PA 2014 70120, filed on Mar. 12, 2014. The disclosures of the above-referenced applications are hereby expressly incorporated by reference in their entireties.

TECHNICAL FIELD OF THE INVENTION

The present invention relates to a system and a corresponding method for estimating the respiratory drive of mechanically ventilated patients. More particularly, for apportioning this respiratory drive into one, or more, components related to chemical drive—i.e. the drive due to the chemoreceptor response—and/or muscular drive—i.e. the contraction of respiratory muscles, for example the diaphragm.

BACKGROUND OF THE INVENTION

Patients residing at the intensive care unit typically receive mechanical support for their ventilation. Selecting the appropriate level of mechanical ventilation is not trivial, and it has been shown that appropriate settings can reduce mortality [1].

Notice that a device or system capable of performing mechanical ventilation is sometimes called an artificial breathing machine, a life support device, or, more popularly, a respirator.

Typically, patients are ventilated using "support" modes. In these modes, patients have some respiratory drive and try to breathe themselves, with the patient then being "supported" with extra inspiratory volume or pressure. The patient's respiratory drive is controlled, primarily, by two factors.

The first factor is the signalling from the brain to the respiratory muscles that they should contract such that a breath is taken. This signaling is due to a number of factors but paramount in these is the chemical signaling by the chemoreflex system. Adverse changes in oxygen, carbon dioxide and acid levels of blood and cerebral spinal fluid (CSF) are detected by the body chemoreceptors, which signal the brain to change the rate and depth of breathing. In health this signaling will be appropriate to normalize levels of oxygen, carbon dioxide and acidity of the blood and CSF. In disease, or in other situations such as the administration of opioids and other drugs, chemoreceptor response may be reduced, and signaling insufficient. The chemical response to breathing is also modified by metabolism, such that a greater respiratory drive will be present in situations of higher $CO_2$ production; and in situations where the acid-base status of blood or CSF is acutely or chronically changed. For example, the chronic changes in the buffering properties of CSF in patients with chronic lung disease are well known to reduce chemical drive to breathing via central chemoreceptor response.

The second factor is the nature of the muscles. In health, signals from the brain to the respiratory muscles that a breath is required, would result in contraction of the respiratory muscles by the appropriate amount to ensure ventilator volumes, which normalize levels of oxygen, carbon dioxide and acidity of the blood and CSF. In disease, the respiratory muscles may be weakened or tired and as such unable to contract the appropriate amount.

The degree to which patients on mechanical ventilation should be supported depends upon their respiratory drive i.e. their own capability to control respiration. Patients with reduced drive will require extra support through greater volume or pressure levels. Patients with more normal levels of drive could receive reduced support, potentially enabling then to be weaned from mechanical ventilation more quickly. As weaning takes up a large portion of the time spent on mechanical ventilation[2], rapid appropriate weaning may be very beneficial. Hence, improved methods for estimating respiratory drive would be advantageous.

A deeper understanding of the reasons for reduced respiratory drive could also be beneficial. Reduced chemical drive could lead the doctor to consider reducing opioid therapy. Reduced muscular drive could lead the doctor to consider mobilisation of the patient. Hence, improved methods for apportioning respiratory drive to components related to chemical and/or muscular drive would be advantageous.

US patent application 2010/0228142 (invented by Christer Sinderby, assigned to Maquet Critical Care) discloses a method for determining dynamically a respiratory feature in a spontaneously breathing patient receiving mechanical ventilatory assist. The method comprises: modifying a level of mechanical ventilatory assist to the patient, measuring an airway pressure, detecting a change of gradient of the measured airway pressure and determining the respiratory feature based on the measured airway pressure upon detecting the change of gradient of the airway pressure. Furthermore, the method also comprises: measuring a respiratory neural drive of the patient and detecting a lowest level of the measured respiratory neural drive for determining the respiratory feature based on the detected lowest level of respiratory neural drive. An inherent disadvantage by this method is the need for measuring neural drive by an electrode in the diaphragm which is typically inserted into the oesophagus.

Hence, an improved way of estimating respiratory drive would be advantageous, and in particular a more efficient and/or reliable way of estimating respiratory drive would be advantageous.

SUMMARY OF THE INVENTION

A system and a corresponding method are presented where baseline values of, or changes in the values of volume support or pressure support, in a mechanically ventilated patient, and measurement of the response in ventilator parameters, such as respiratory frequency, are used to estimate the patient's respiratory drive, and preferably to apportion this drive into one, or more, components related to chemical and muscular response. In this way, a greater understanding of the patient can be obtained during mechanical ventilation, which may improve diagnosis and the selection of mechanical ventilator settings.

Thus, an object of the present invention relates to a system and a method for estimating the total respiratory drive of a patient from changes in mechanical ventilator settings.

Thus, one object of the invention relates to a system and a method for apportioning a component of the respiratory drive due to chemical response from chemoreceptors.

Thus, a further object of the invention relates to a system and a method for apportioning a component of the respiratory drive due to muscular response for the respiratory muscles.

In a first aspect, the present invention relates to a mechanical ventilation system for respiration aid of an associated patient, the system being adapted for estimating one, or more, components of the respiratory drive (R_DRIVE) of said patient, the system comprising:

- ventilator means (VENT) capable of mechanical ventilating said patient with air and/or one or more medical gases,
- control means (CON), the ventilator means being controllable by said control means by operational connection thereto, and
- measurement means (M_G) arranged for measuring the respiratory feedback of said patient in the expired gas in response to the mechanical ventilation, the measurement means being capable of delivering first data (D1) to said control means, wherein the control means is capable of operating the ventilation means by providing ventilatory assistance so that said patient is at least partly breathing spontaneously, and, when providing such ventilatory assistance, the control means being capable of changing one, or more, volume and/or pressure parameters (Vt_SET) of the ventilator means so as to detect changes in the respiratory feedback of said patient by the measurement means, the control means further being arranged for receiving second data (D2), preferably obtainable from blood analysis of said patient, said second data being indicative of the respiratory feedback in the blood of said patient, the control means being adapted for using:

- the first data (D1) indicative of changes of respiratory feedback in expired air, and
- the second data (D2) indicative of the respiratory feedback in the blood, in a physiological model (MOD) capable of estimating one, or more, components (R_MUSC, R_CHEM) of the total respiratory drive (R_DRIVE) for the patient.

The principle of the invention presented here is that measurement of changes ventilation frequency or volume in response to changes ventilator support settings can be used, in combination with mathematical physiological models, to identify chemoreceptor drive, muscular drive and/or the total respiratory drive which is beneficial to obtain for diagnostic and/or curative purposes.

Advantageously, the physiological model (MOD) may comprise a component of the total respiratory drive being indicative of muscular response (R_MUSC). This is an advantage because previously the muscular response could be difficult to measure or evaluate. Alternatively or additionally, the physiological model (MOD) may comprise a component of the total respiratory drive being indicative of chemical response (R_CHEM), preferably a subcomponent indicative of the central chemical response and a subcomponent indicative of the peripheral chemical response. The chemical response of the respiratory drive is typically the dominating factor and is therefore important to evaluate. Beneficially, the control means may be arranged for estimating both the muscular response (R_MUS) and chemical response (R_CHEM) forming part of the total respiratory drive (R_DRIVE).

In another embodiment of the mechanical ventilation system, the measurement means and the control means may be further arranged to measure an indication of muscular response (R_MUSC), such as by estimating or obtaining muscular drive from other measurement means or sources (e.g. previous values), such as an electrical measurement of the diaphragm, or similar.

In an embodiment, the control means may be arranged for estimating the muscular response (R_MUS) and chemical response (R_CHEM) by initially assuming one of the two responses; muscular response (R_MUS) or chemical response (R_CHEM), being a certain approximately constant level, preferably a normal level for said patient depending on the medical history and/or condition of the patient, and then subsequently iteratively solving for the other response, e.g. assuming normal muscular response and then solve for the chemical response as it will be explained below. In one particular embodiment of this, the mechanical ventilation system may assume that the muscular response is initially constant, preferably a normal level for said patient, and the chemical response may then be estimated, the estimated chemical response being subsequently applied for modelling a respiratory feedback to be compared with a measured respiratory feedback of the patient, this feedback being characterised by for example changes in respiratory volume or frequency, or measures of oxygenation or acid base-status of blood, or respiratory gasses. Any deviation between model simulated and measured feedback being an absolute or relative measure for an inadequate response capability of the patient. The said inadequate response capability of the patient may at least be a measure of the fatigue of the patient, though the inadequate response capability of the patient could also be interpreted to be a measure, or a component, of other reasons for poor respiratory muscle function such as medication with for example muscle relaxants, or other medications which reduce respiratory response through action on non-chemoreceptor mechanisms.

In one embodiment, the second data (D2) used in the physiological model (MOD) may be indicative for oxygenation and/or acid-base status of the blood, e.g. pHa, preferably being related to the influence of the acid-base status on the cerebrospinal fluid (CSF). In another embodiment, the second data (D2) used in the physiological model (MOD) may, alternatively or additionally, be indicative for the metabolism of said patient, preferably the tissue production of carbon dioxide ($CO_2$).

In one particular embodiment, the physiological model (MOD) capable of estimating one, or more, components of the total respiratory drive (R_DRIVE) for the patient may be operationally connected to a medical decision support system (DSS), preferably for application in mechanical ventilation. The DSS could be applied in connection with treatment plan, for therapy, and/or for diagnosis of the patient. As an example, the DSS could be the so-called INVENT system co-developed by one of the present inventors, cf. reference [5] and [6], these references being hereby incorporated by reference in their entirety.

In another particular embodiment, the measurement means (M_G) may be arranged for measuring one or more of the following parameters consisting of: respiratory frequency (RR) or, equivalently, duration of breath (including duration of inspiratory or expiratory phase), and expiratory carbon dioxide levels ($FECO_2$), fraction of carbon dioxide in expired gas at the end of expiration, ($FE'CO_2$), partial pressure of carbon dioxide in expired gas ($PECO_2$), partial pressure of carbon dioxide in expired gas at the end of expiration ($PE'CO_2$), or equivalents thereof and/or combinations thereof. Other parameters applicable for respiratory response or feedback by a patient measurable in the expired air may also be applied within the context of the present invention once the general principle and teaching of the invention has been appreciated by the skilled person.

In another embodiment, the second data (D2), which may be obtainable from blood analysis (M_B) of said patient (P), may be one or more parameters consisting of: arterial blood pH (pHa), pressure of carbon dioxide level ($PaCO_2$), optionally measured transcutaneously ($PtcCO_2$), oxygen saturation of arterial blood ($SaO_2$), pressure of oxygen in arterial blood ($PpO_2$), or equivalents thereof and/or combinations thereof. Other parameters applicable, estimated or measurable in blood of a patient may also be applied within the context of the present invention once the general principle and teaching of the invention has been appreciated by the skilled person.

Particularly, the present invention is advantageous in that the respiratory drive may be estimated without using a measurement of the electrical activity of the diaphragm of the patient, cf. US patent application 2010/0228142 where this is performed.

In a beneficial embodiment, the control means (CON) may be capable of changing the level from one value to another value in one, or more, volume and/or pressure parameters of the ventilator means (Vt_SET) so as to detect the subsequent changes in the respiratory feedback of said patient by the measurement means. Thus, the changes of ventilator setting are made and afterwards the respiratory feedback of the patient is measured.

Beneficially, the control means may be alternatively be capable of performing a change in one, or more, volume and/or pressure parameters of the ventilator means (Vt_SET) so as to detect associated changes in the respiratory feedback of said patient by the measurement means while performing said change. Thus, the changes of Vt_SET are made while changes in respiration are simultaneously measured.

In one embodiment, wherein the control means may be capable of changing one, or more, volume and/or pressure parameters of the ventilator means by changing the inspiratory volume (Vt_SET) and/or the inspiratory pressure set by the ventilator means. It is important to distinguish between the settings for pressure or volume for the mechanical ventilator, and, on the other hand, the actual volume inhaled or expired by the patient, as it will be understood by a person skilled in mechanical ventilation of patients.

In a second aspect, the present invention relates to method for operating a mechanical ventilation system for respiration aid of an associated patient, the method being adapted for estimating one, or more, components of the respiratory drive (R_DRIVE) of said patient, the method comprising:
  providing ventilator means (VENT) capable of mechanical ventilating said patient with air and/or one or more medical gases,
  providing control means (CON), the ventilator means being controllable by said control means by operational connection thereto, and
  providing measurement means (M_G) arranged for measuring the respiratory feedback of said patient in the expired gas in response to the mechanical ventilation, the measurement means being capable of delivering first data (D1) to said control means,
wherein the control means is capable of operating the ventilation means by providing ventilatory assistance so that said patient is at least partly breathing spontaneously, and, when providing such ventilatory assistance, the control means being capable of changing one, or more, volume and/or pressure parameters (Vt_SET) of the ventilator means so as to detect changes in the respiratory feedback of said patient by the measurement means,
the control means further being arranged for receiving second data (D2), preferably obtainable from blood analysis of said patient, said second data being indicative of the respiratory feedback in the blood of said patient,
the control means being adapted for:
  applying the first data (D1) indicative of changes of respiratory feedback in expired air, and
  applying the second data (D2) indicative of the respiratory feedback in the blood,
in a physiological model (MOD) capable of estimating one, or more, components (R_MUSC, R_CHEM) of the total respiratory drive (R_DRIVE) for the patient.

In a third aspect, the present invention relates to a computer program product being adapted to enable a computer system comprising at least one computer having data storage means in connection therewith to control a ventilation system according to the first and/or second aspect. Thus, this aspect of the invention may differ from the method of the second aspect in that the third aspect is directed to controlling and/or cooperating with the ventilator means (VENT), the control means (CON), and measurement means (M_G) i.e. instead of providing them.

This aspect of the invention is particularly, but not exclusively, advantageous in that the present invention may be accomplished by a computer program product enabling a computer system to carry out the operations of the ventilation system of the first aspect of the invention when down- or uploaded into the computer system. Such a computer program product may be provided on any kind of computer readable medium, or through a network.

The individual aspects of the present invention may each be combined with any of the other aspects. These and other aspects of the invention will be apparent from the following description with reference to the described embodiments.

BRIEF DESCRIPTION OF THE FIGURES

The method according to the invention will now be described in more detail with regard to the accompanying figures. The figures show one way of implementing the present invention and is not to be construed as being limiting to other possible embodiments falling within the scope of the attached claim set.

DETAILED DESCRIPTION OF THE INVENTION

Figure 1:
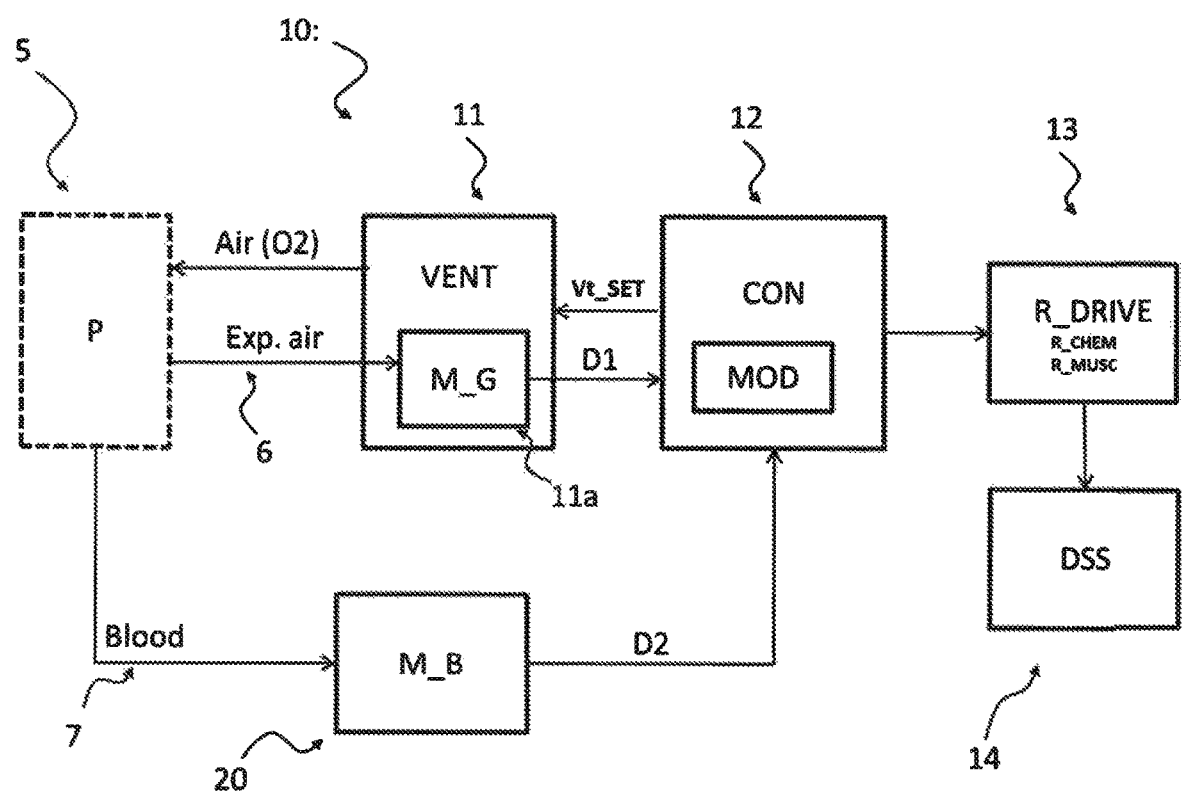
FIG. 1 is a schematic drawing of a mechanical ventilation system according to the present invention.

FIG. 1 is a schematic drawing of a mechanical ventilation system 10 for respiration aid of an associated patient 5, P, the system being adapted for estimating the respiratory drive R_DRIVE of the patient.

The system comprises ventilator means 11, VENT capable of mechanical ventilating said patient with air and/or one or more medical gases, e.g. oxygen and/or nitrogen. Conventional ventilator systems currently available may be modified or adapted for working in the context of the present invention. Furthermore, control means 12, CON is comprised in the system 10, the ventilator means 11 being controllable by said control means 10 by operational connection thereto, e.g. appropriate wirings and interfaces as it will be appreciated by the skilled person working with mechanical ventilation.

Additionally, measurement means 11a, M_G are arranged for measuring the respiratory feedback of said patient in the expired gas 6 in response to the mechanical ventilation, e.g. respiratory frequency or fraction of expired carbon dioxide commonly abbreviated $FECO_2$, cf. list of some well-known abbreviations below. The measurement means are shown as forming part of the ventilator means 11, but could alternatively form an independent entity with respect to the ventilator means without significantly change the basic principle of the present invention. The measurement means M_G are capable of delivering first data D1 to the control means 12 CON by appropriate connection, by wire, wirelessly or by other suitably data connection.

The control means 12 CON is also capable of operating the ventilation means by providing ventilatory assistance so that said patient 5 P is at least partly breathing spontaneously, and, when providing such ventilatory assistance, the control means being capable of changing one, or more, volume and/or pressure parameters Vt_SET of the ventilator means so as to detect changes in the respiratory feedback in general of the patient by the measurement means M_G.

The control means is further being arranged for receiving second data D2, preferably obtainable from blood analysis of said patient performed by blood measurement means M_B 20, the second data being indicative of the respiratory feedback in the blood of said patient, e.g. pHa, PACO2, PA02 etc. Notice that the by blood measurement means M_B 20 is not necessarily comprised in the ventilator system 10 according to the present invention. Rather, the system 10 is adapted for receiving second data D2 from such an entity or device as schematically indicated by the connecting arrow. It is however contemplated that a blood measurement means M_B could be comprised in the system 10 and integrated therein. In this embodiment, the mechanical ventilator system comprises at least the ventilator means VENT 10, the measurement means M_G 11a, and the control means CON 12. The physiological model MOD is implemented on the control means, e.g. in an appropriate computing entity or device.

In one variant of the invention, the second data D2 could be estimated or guessed values being indicative of the respiratory feedback in the blood of said patient, preferably based on the medical history and/or present condition of the said patient. Thus, values from previously (earlier same day or previous days) could form the basis of such estimated guess for second data D2.

The control means is adapted for using both the first data D1 indicative of changes of respiratory feedback in expired air 6, and the second data D2 indicative of the respiratory feedback in the blood 7, in a physiological model MOD capable of estimating one, or more, components of the total respiratory drive R_DRIVE for the patient 6 as schematically indicated in the box 13.

The respiratory drive R_DRIVE may be outputted to an appropriate human-machine interface 13 for displaying the result, e.g. a computer with a screen therefore. Alternatively or additionally, the respiratory drive output R_DRIVE and/or its components, may be communicated to a decision support system DSS 14 for use in connection with mechanical ventilation of patients, optionally for treatment and/or diagnostic purposes.

Figure 2:
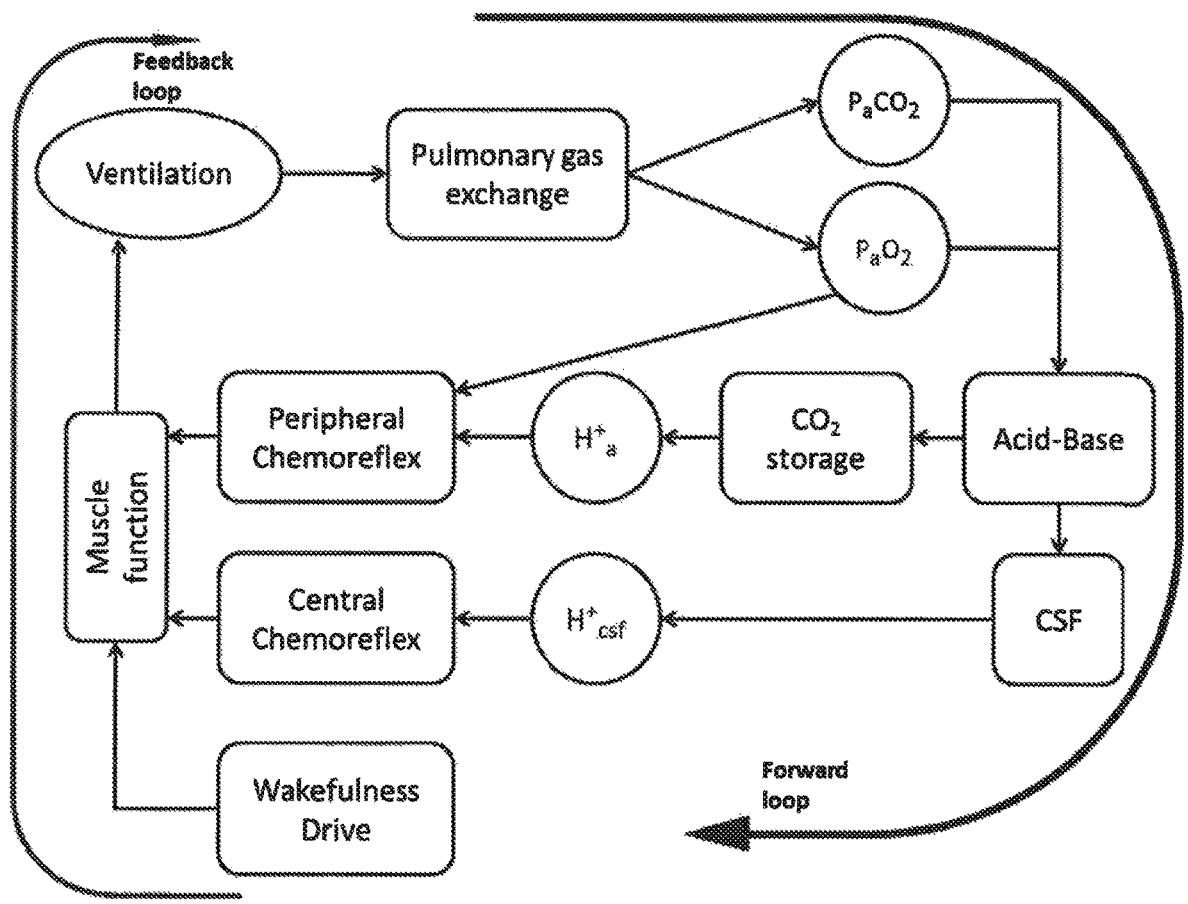
FIG. 2 is a schematic flow chart of a physiological model applied in the present invention.

The principle of this invention is further exemplified in FIGS. 2 and 3. FIG. 2 illustrates an example of the structure a physiological model used in the method. It consists of model components representing the gas exchange of the lungs and the acid-base chemistry of the blood, components representing the acid-base of cerebrospinal fluid (CSF) and the resulting chemical respiratory drive, and the net effect of this chemical drive ventilation according to the action of respiratory muscles. Some of these models exist in the scientific literature [3,4], which are hereby incorporated by reference in their entirety, and the advantage of the present invention is not in the formulation of such models as such but in their use, combined with changes in ventilation to determine total respiratory drive, and/or any of the components related to chemical and muscular drive.

FIG. 3 illustrates the model simulated response of a patient to changes in ventilator support, in this case volume support, represented as the volume of ventilation provided to the patient per breath (Vt), i.e. the variable on the x-axis of each of the subfigures in FIG. 3. Alveolar ventilation (VA) could be plotted instead of tidal ventilation with no apparent differences in the method. In particular it simulates the expected respiratory frequency (3a,d), arterial pH (3b,e), and end tidal carbon dioxide ($FE'CO_2$) (3c,f) levels at different levels of volume support (Vt). This response profile can be used to determine the total respiratory drive, and the components of chemical and muscular response. It is important to note that two factors separate this approach from those presented previously. The first is that no measure of the electrical activity of the diaphragm is used to assess the muscular drive to breathing. The second is that the simulated response to changes in ventilator support due to chemical drive can be accounted for by several physiological factors. This is only possible because of the physiological model, including factors contributing to the chemical drive describing: metabolism, and in particular the tissue production of $CO_2$; the acid-base status of blood which modifies peripheral chemoreceptor drive; and the acid base status of CSF which modifies central chemoreceptor drive. These aspects have not been accounted for previously, e.g. US patent application 2010/0228142 which is based upon diaphragm electrical activity. FIGS. 3a, 3b and 3c of the present application, illustrate two different situations of a normal (solid line) and reduced (dashed line) total respiratory drive. Reducing the total respiratory drive modifies the position of the curves and lines representing these three variables. Estimation of the parallel shift of the three solid lines to the three dashed lines provides data which enables estimation of changes in the total respiratory drive.

Figure 3A:
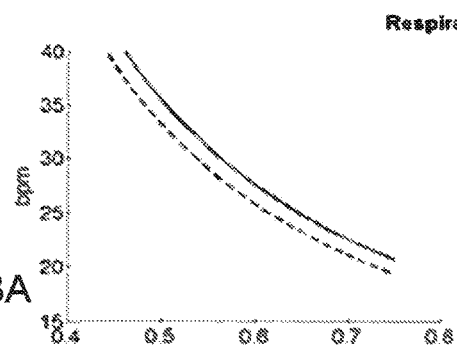
FIGS. 3A-3F are model simulated responses of a patient to changes in ventilator support.
Figure 3D:
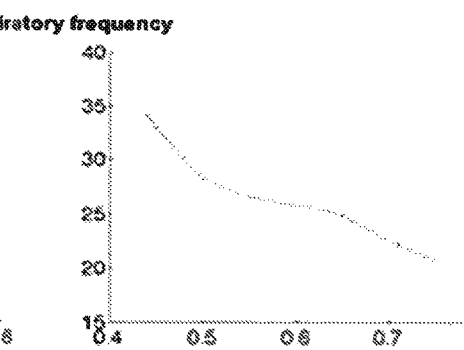
Figure 3B:
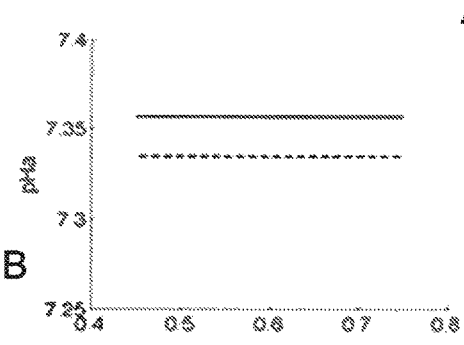
Figure 3E:
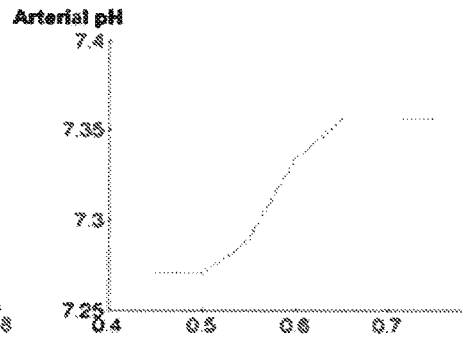
Figure 3C:
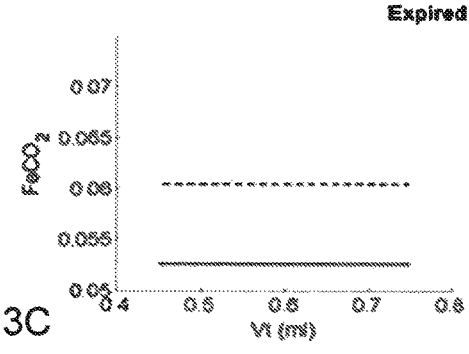
Figure 3F:
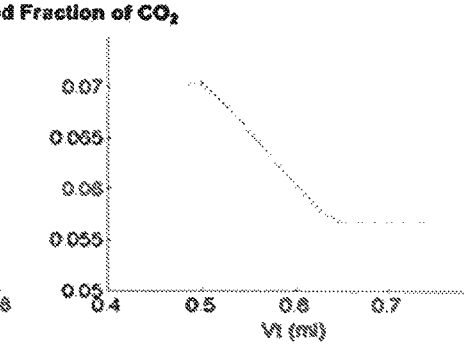

The apportionment of total respiratory drive to chemical and muscular components can be seen as the difference between FIGS. 3a-c and 3d-f. In 3a-c, i.e. left hand side of FIG. 3, the patient's muscle strength is normal, and the patient can respond adequately to reduction in Vt such that respiratory frequency increases and pH and $FE'CO_2$ remain constant. This pattern of response is consistent with the total respiratory drive being explained by changes in chemical response only. In this case the alveolar ventilation predicted by the chemical drive model (VAexp, FIG. 6) is equivalent to the alveolar ventilation of the patient (VA, FIG. 6). FIGS. 3d-3f, i.e. the right hand side of FIG. 3 illustrate the situation where patients muscle strength cannot respond adequately to reduction in volume support and respiratory frequency increases only partially, pH falls and FE'CO$_2$ increases. The alveolar ventilation predicted by the chemical drive (VAexp, FIG. 6) cannot be maintained by the muscles such that the true alveolar ventilation is lower and as a consequence pH falls and FE'CO$_2$ increases. This can be implemented by multiplying the alveolar ventilation predicted by the chemical model with a fraction (fM, FIG. 6) between 0 and 1, where 0 represents no muscle action and 1 muscle action sufficient to allow alveolar ventilation consistent with the respiratory drive. The quantification of the change in total respiratory drive and the components due to chemical and muscular response can be performed either via shifts in the measured curves or by analysing the responses illustrated in FIG. 3 using mathematical models, similar in structure to FIG. 2 and in details to FIG. 6. Estimation of mathematical model parameters can then provide quantification of total respiratory drive and in addition chemical drive and/or muscular drive. It is thus to be understood that any combination of the total drive, the chemical drive (incl. sub-components) and the muscular drive (incl. sub-components) may be provided as a result of applying the present invention as described above, the drive components not being provided as results may possibly be applied as intermediate result(s), e.g. the total respiratory drive may be an intermediate result for finding the components of muscular drive and/or chemical drive.

The overall principle of the method is then that changes in support mode settings which result in changes in tidal volume and respiratory frequency and or acid base status of blood or respiratory gasses can be used to estimate respiratory drive, and optionally apportion that to components related to chemical and muscular drive.

The invention thus relates to a method for determining respiratory drive and apportioning this to components related to chemical and muscular response.

The invention comprises measuring the level of ventilation volume or pressure, and one or more of the following variables respiratory frequency, arterial blood pH or carbon dioxide level, and expiratory carbon dioxide levels.

The invention further comprises changing ventilation volume or pressure and evaluating the changes in the following variables respiratory frequency, arterial blood pH or carbon dioxide level.

The method further comprises analysis of these data in terms of mathematical models or curve shifts to determine respiratory drive.

The method further comprises analysis of these data in terms of mathematical models or curve shifts to determine the component of respiratory drive due to chemical response.

The method further comprises that measurements of metabolism and acid-base status of the blood or CSF can be accounted for in the component of respiratory drive due to chemical response.

The method further comprises analysis of these data in terms of mathematical models or curve shifts to determine the component of respiratory drive due to response of the muscular system involved in breathing.

Advantageously, the level of carbon dioxide in respiratory gas may be provided by measurements of FECO$_2$, PECO$_2$, FE'CO$_2$, PE'CO$_2$ or other equivalent measures available to the skilled person.

The present invention may be beneficially applied when the individual is a normal person, a person under mechanical ventilation in general, or suffers from one or more respiratory diseases or abnormalities, including primary and secondary lung diseases, such as chronic obstructive pulmonary disease (COPD), acute lung injury, acute respiratory distress syndrome, pulmonary edema, or asthma. Other related or similar diseases/conditions for which the present invention may be advantageously applied are also contemplated.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

It should be noted that embodiments and features described in the context of one of the aspects of the present invention also apply to the other aspects of the invention.

The invention will now be described in further details in the following non-limiting examples.

Example

Figure 4A:
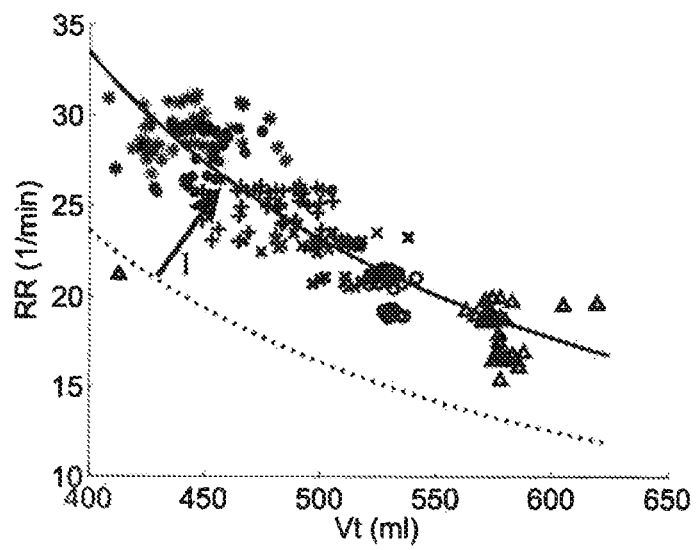
FIGS. 4A-4C show three graphs using data collected from a single patient showing the results of the present invention in the graphs.
Figure 4B:
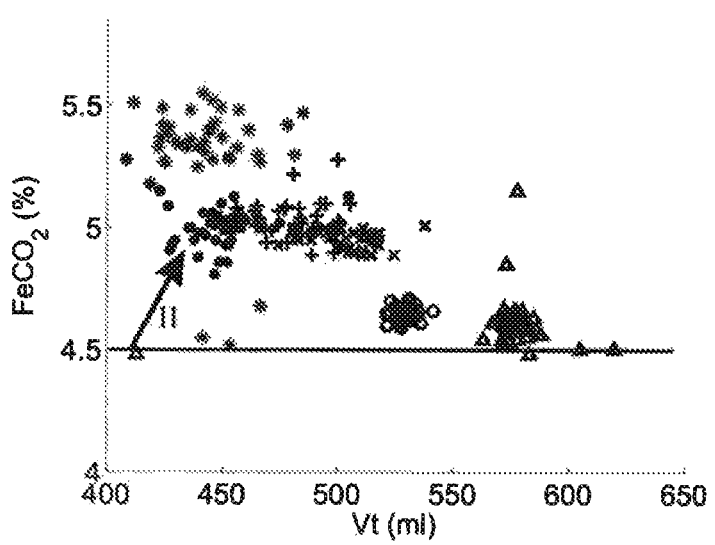
Figure 4C:
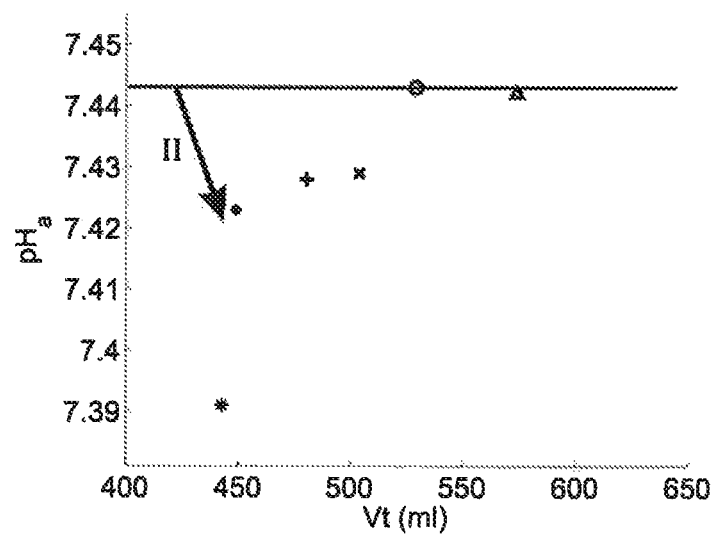

FIGS. 4 and 5 exemplify the technique using data collected from two patients (one for each figure). In FIG. 4, plots are shown of changes in tidal volume (Vt) against A) respiratory frequency, B) end tidal CO$_2$ and C) arterial pH. The dashed curve in FIG. 4A represents the model simulated response of these variables assuming normal muscular and chemical response, normal values of metabolism, e.g. rate of tissue CO$_2$ production, and normal values of the acid-base status of blood and CSF. Stars, solid circles, crosses, diagonal crosses, open circles and triangles on plots 4A-C represent data collected at different values of Vt, with each symbol representing a different value of ventilator setting on the ventilator, Vt_SET. It should be noted this data has been collected and plotted with volume as a variable, but in clinical practise the pressure is often applied as the variable instead. This is however equivalent as the skilled person will understand, and does not change the overall principle and teaching of the present invention.

Solid curves on plots 4A-C represent model simulations when the chemical response is adapted to the individual patient, but assuming normal muscular response. This adaptation to chemical response includes: a) inputting the rate of $CO_2$ production into the physiological model for that individual patient, where $CO_2$ production can be measured from respiratory gas composition and flow; b) inputting the acid-base status of blood into the model and from this calculating the state of CSF acid-base status, where acid-base status is measured, for example, from a blood sample. In addition any factors in the response is not explained by changes in $CO_2$ production or abnormal acid-base status are then accounted for by fitting the physiological mathematical model to the measured data shown on FIG. 4A. This model fitting can be performed using standard least-square techniques where model parameters such as those describing thresholds or gains in central or peripheral chemical drive are adjusted until the model provides a best fit to the data as the minimum sum of squared differences between model predictions and measured data. This model fitting can be performed for data collected at a single setting of mechanical ventilation, or over a data set collected at several different settings as illustrated by each of the symbols on FIG. 4A.

In FIG. 5, plots are shown of changes in tidal volume (Vt) against (a and e) respiratory frequency, and (b and f) arterial pH, and (c and g) end tidal $CO_2$. The dashed curve in all subplots of FIG. 5 represent the model simulated response of these variables assuming normal muscular and chemical response, normal values of metabolism, e.g. rate of tissue $CO_2$ production, and normal values of the acid-base status of blood and CSF. Triangles, open circles, diagonal crosses, vertical crosses, diamonds and stars represent data collected or model simulations at different values of Vt, with each symbol representing a different value of ventilator setting on the ventilator, Vt_SET. Measured data points are connected with solid lines, and model simulated points are connected with dotted lines. It should be noted these data have been collected and plotted with volume as a variable as either tidal volume or alveolar ventilation, but in clinical practise pressure is often applied as the variable instead. This is however equivalent as the skilled person will understand, and does not change the overall principle and teaching of the present invention. Error bars are represented where points are repeated measures. For FIGS. 5a-c these figures represent model simulations when the chemical response is adapted to the individual patient, but assuming normal muscular response (fM=1). This adaptation to chemical response includes: a) inputting the rate of $CO_2$ production into the physiological model for that individual patient, where $CO_2$ production can be measured from respiratory gas composition and flow; b) inputting the acid-base status of blood into the model and from this calculating the state of CSF acid-base status, where acid-base status is measured, for example, from a blood sample. In addition any factors in the response is not explained by changes in $CO_2$ production or abnormal acid-base status are then accounted for by fitting the physiological mathematical model to the measured data shown on FIGS. 5 a-c. This model fitting can be performed using standard least-square techniques where model parameters such as those describing thresholds or gains in central or peripheral chemical drive are adjusted until the model provides a best fit to the data as the minimum sum of squared differences between model predictions and measured data. This model fitting can be performed for data collected at a single setting of mechanical ventilation, or over a data set collected at several different settings as illustrated by each of the symbols on FIGS. 5 a-c. It can be seen for this patient that fitting the chemical drive model alone results in simulations (symbols connected with dotted lines) which match measurements (symbols connected with solid lines) very well for the highest 4 levels of Vt, i.e. for levels represented by triangles, open circles, diagonal crosses, and vertical crosses. Data describing the lowest 2 levels of Vt (symbols starts and diamonds), where the patient is likely most stressed, are not described well by the chemical model with model simulated of respiratory frequency too high, model simulated pHa too high and model simulated FetCO2 too low.

FIG. 5 e-g includes model simulations (symbols connected with dotted lines) when the chemical response is adapted to the individual patient, along with adaptation to muscular response. It can be seen for this patient that fitting the chemical drive model and muscular response results in simulations (symbols connected with dotted lines) which match measurements (symbols connected with solid lines) at all levels of Vt. To do so the alveolar ventilation calculated by the chemical model is modified by a constant fraction. This fraction is shown in FIG. 5d for each of the values of Vt. For the highest 4 levels of Vt, i.e. for levels represented by triangles, open circles, diagonal crosses, and vertical crosses the value of the fraction (fM) is 1, indicating no correction is required. For the lowest 2 levels of Vt (stars and diamonds), where the patient is likely most stressed, the alveolar ventilation calculated by the chemical model is reduced, requiring a value of the fraction fM=approximately 0.7 to account for muscle fatigue.

Patients

These cases represent mechanically ventilated patients admitted to an intensive care unit Informed consent was obtained and the study was approved by the local Ethics Committee.

Data Analysis and Results

The model of chemical drive was adapted to the patient to describe the respiratory frequency, end tidal CO2 and arterial pH changes following changes in Vt as described above accounting for $CO_2$ production, acid-base status in blood and CSF and by fitting the model to the data to estimate parameters describing the threshold and gain of central chemoreceptor response. The shift illustrated by the arrow in FIG. 4a (labelled I) represents the change in chemical respiratory drive from normal seem in this patient due to all these factors in the mathematical model.

Since the solid curves represent model simulations when the chemical response is adapted to the individual patient, but assuming normal muscular response, then the shift illustrated by the arrows in plots 4b and 4c, and labelled II, represents changes in pH and $PCO_2$ characteristic of muscle fatigue and hence reduced muscle drive. These shifts can be represented graphically as here, or by using values of physiological model parameters. These parameters can, for example, describe weighting of the calculated chemical drive so as to reduce the effect of chemical response.

Figure 5A:
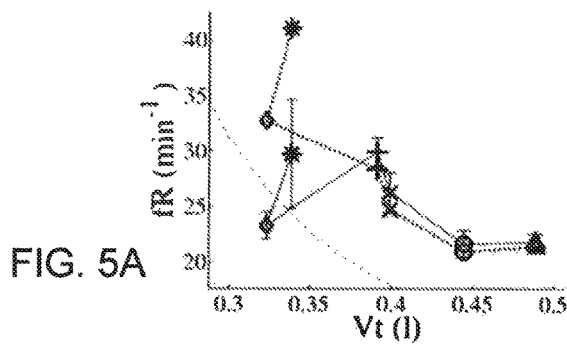
FIGS. 5A-5G show seven graphs using data collected from a single patient showing the results of the present invention in the graphs.
Figure 5E:
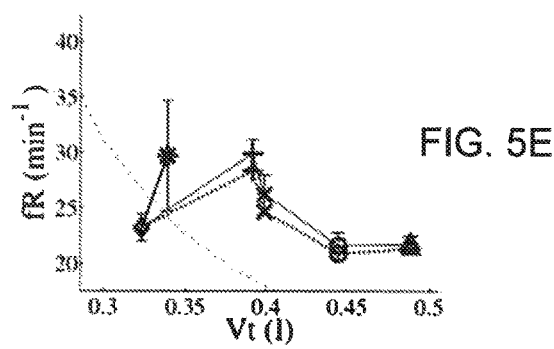
Figure 5B:
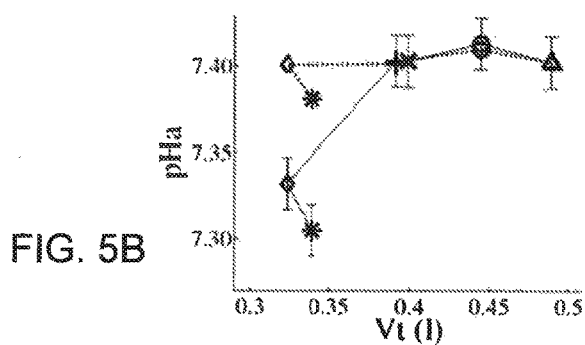
Figure 5F:
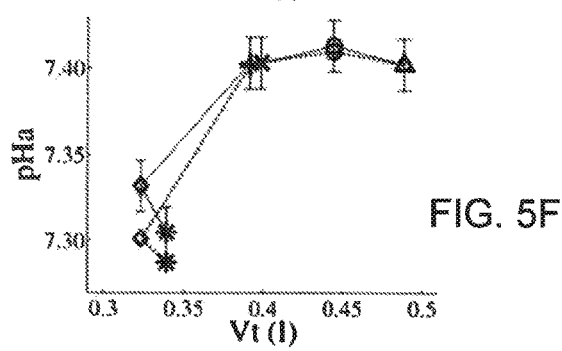
Figure 5C:
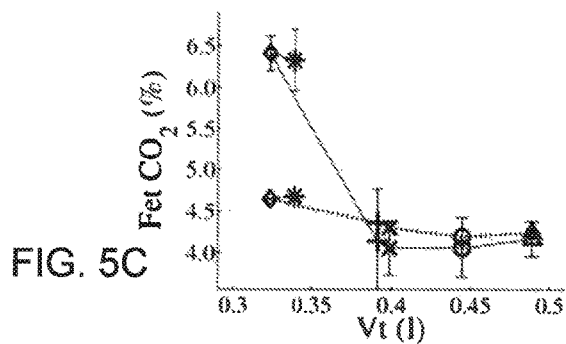
Figure 5G:
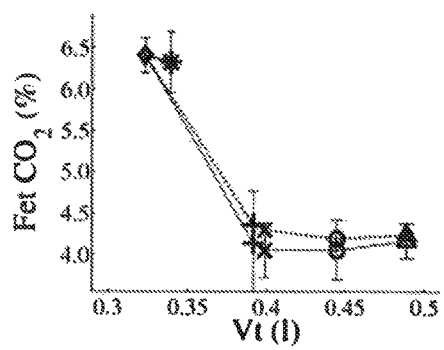
Figure 5D:
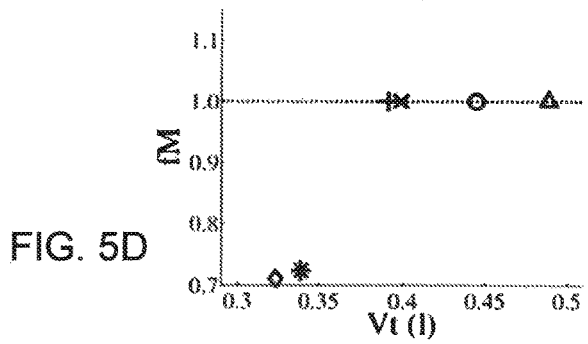

The differences between model simulations (symbols connected with dashed lines) illustrated in FIGS. 5e-g and the dashed lines on these figures represent the changes in chemical respiratory drive from normal and all other factors previously discussed plus the effects of muscle fatigue seen in this patient. The difference between model simulations (symbols connected by dotted lines) in FIGS. 5 a-c and FIGS. 5 e-g represents the differences characteristic of muscle fatigue and hence reduced muscle drive. These differences are quantified in this figure by estimating the factor fM which weighs the expected alveolar ventilation given the chemical drive (VAexp, FIG. 6) to give the patients true alveolar ventilation given their muscular response (VA, FIG. 6).

Conclusion

In these examples, it is shown that data describing the response to changes in respiratory tidal volume can be used to identify changes in respiratory drive, including those that can be apportioned to changes in chemical and muscular response and that chemical drive can be measured components accounting for metabolism and acid-base status and model parameters describing regulation of chemoreceptors.

Figure 6:
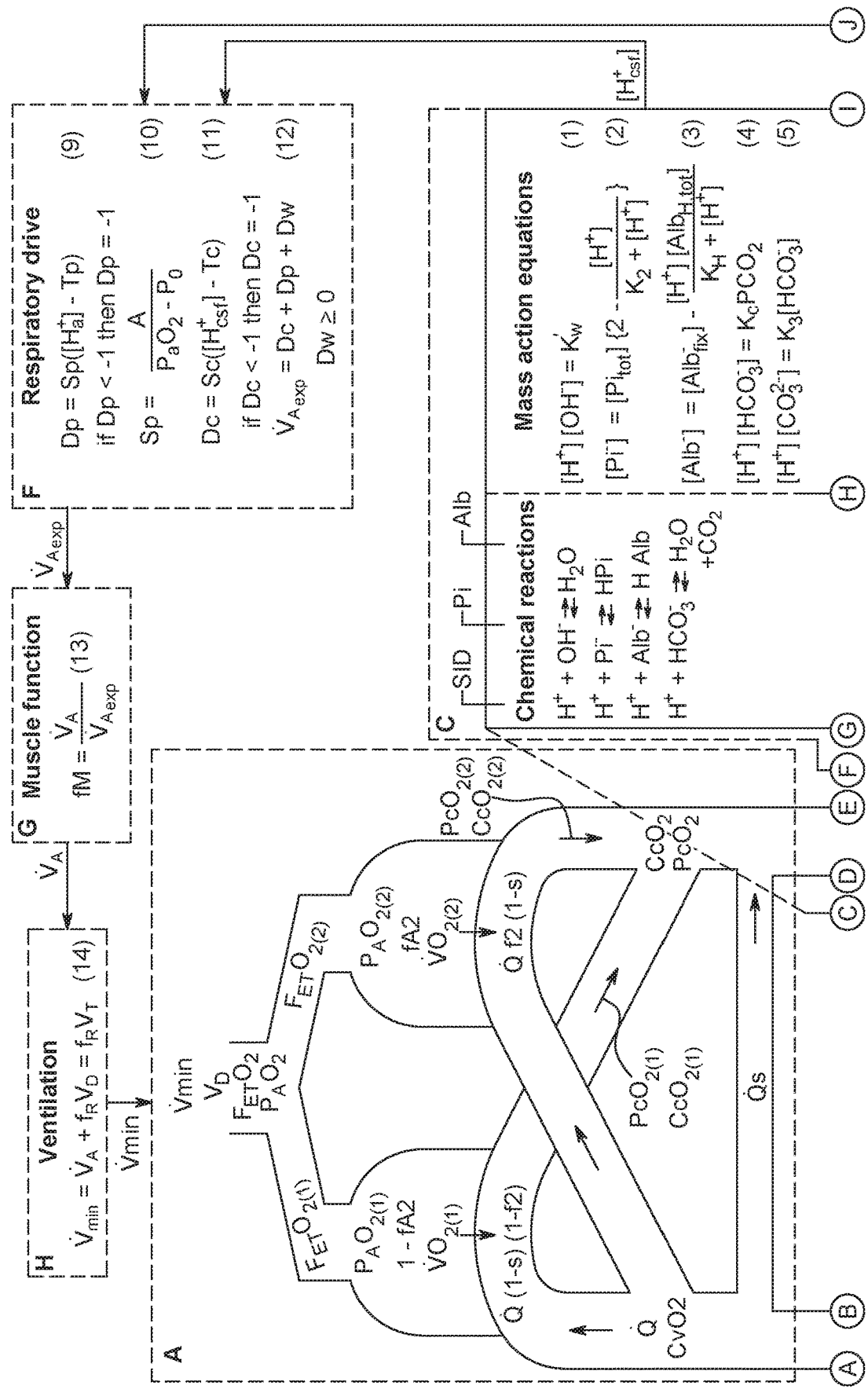
FIG. 6 illustrates the set of mathematical model components of a decision support system (DSS) including the mathematical representation of a physiological model of respiratory control, including the effects of chemical and musculature components of total respiratory drive
Figure 6:
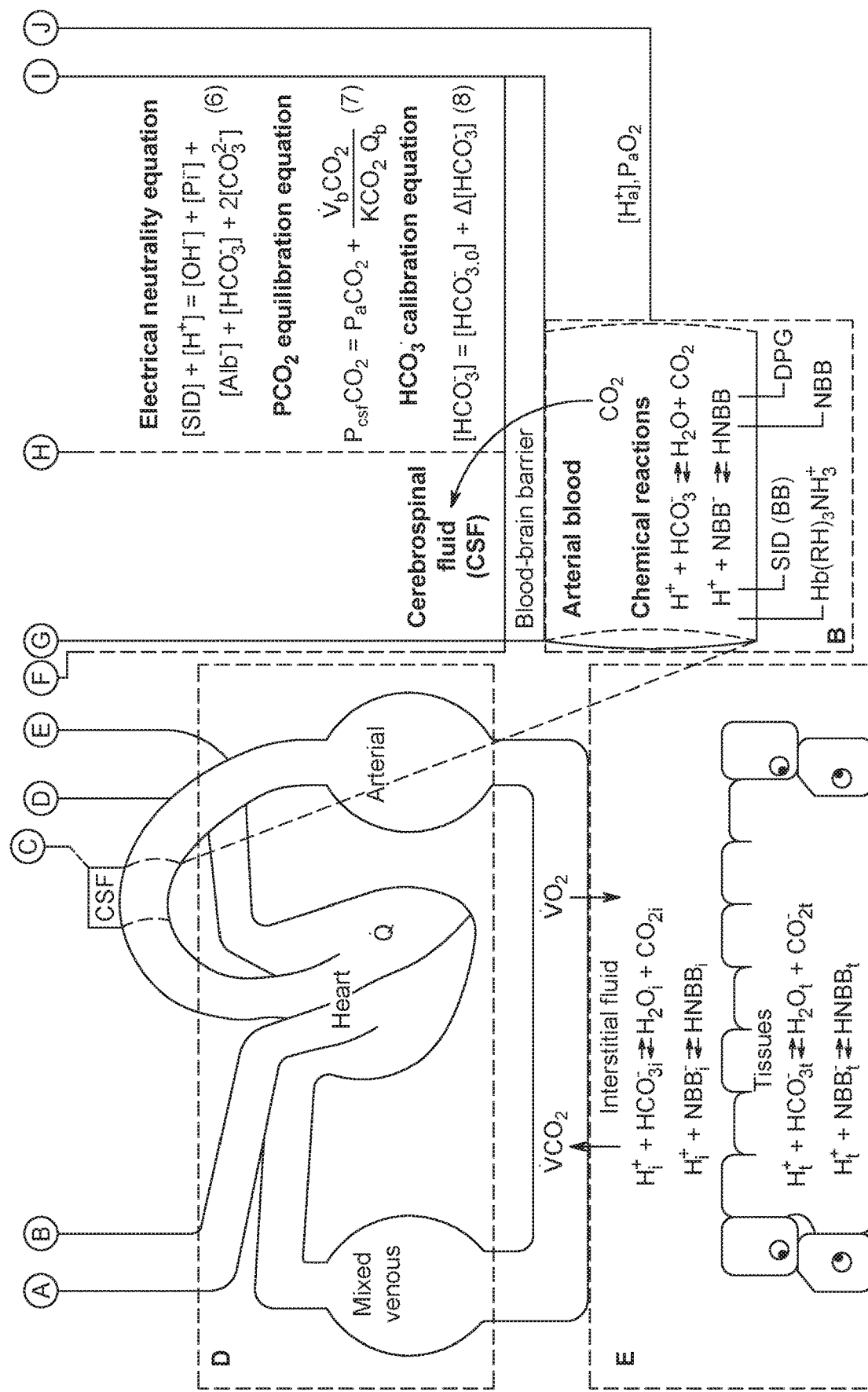

FIG. 6 illustrates the set of mathematical model components of a decision support system (DSS) including the mathematical representation in the form of physiological model of respiratory control and muscle function that may be applied in the context of the present invention. For further background on these models, the skilled person is referred to references [1-6] listed below, which are hereby incorporated by reference in their entirety.

The DSS includes models of: pulmonary gas exchange (A); acid-base status and oxygenation of blood (B); acid-base status of CSF (C); circulation and blood in arterial and mixed venous pools (D); interstitial fluid and tissue buffering, and metabolism (E); chemoreflex model of respiratory control (F); muscular function (G); and ventilation (H).

FIG. 6 illustrates the set of mathematical model components of INVENT including the mathematical representation of respiratory control (A-H). Part A of FIG. 6 illustrates the structure of the model of ventilation and pulmonary gas exchange. Part. B of FIG. 6 illustrates the structure of the model of oxygenation and acid-base status in the blood. Part C of FIG. 6 illustrates Duffin's model of CSF with appropriate model constants [3, 4]. This model includes mass-action equations describing water, phosphate and albumin dissociation plus the formation of bicarbonate and carbonate, and an equation representing electrical neutrality (equations 1-6). In addition, equation (7) is used to describe the equilibration of $PCO_2$ with arterial blood across the blood-brain barrier, Equation (8) is a modification to Duffin's model which allows calibration of the CSF to conditions where blood bicarbonate, and hence buffer base (BB) or strong ion difference (SID) are modified, such as metabolic acidosis where blood bicarbonate is reduced, or chronic lung disease where blood bicarbonate is increased.

The model illustrated in FIG. 6 includes compartments representing $CO_2$ transport and storage including the arterial and venous compartments, and circulation represented as cardiac output (Q) (part D of FIG. 6).

Part E of FIG. 6 illustrates the model of interstitial fluid and tissue buffering, and metabolism included in the system. This includes oxygen consumption ($VO_2$) and carbon dioxide production ($VCO_2$).

Part F of FIG. 6 illustrates the model of respiratory control of Duffin, i.e. equations 9-12. Alveolar ventilation is modeled as a peripheral and central chemoreflex response to arterial and cerebrospinal fluid (CSF) hydrogen ion concentration ($[H^+a]$ and $[H^+csf]$) plus wakefulness drive. Equation (9) describes the peripheral drive (Dp) as a linear function of the difference between $[H^+a]$ and the peripheral threshold (Tp). The slope of tins function (Sp) represents the sensitivity of the peripheral chemoreceptors.

Equation (11) describes central drive (Dc) as a linear function of the difference between $[H^+_{csf}]$ and the central threshold (Tc). The slope of this function (Sc) represents the sensitivity of central chemoreceptors. Equation (12) describes the expected alveolar ventilation as the sum of the two chemoreflex drives and the wakefulness drive (Dw).

Part G of FIG. 6 represents the muscular action on alveolar ventilation. The calculated alveolar ventilation from the respiratory control equations (part F of FIG. 6) is scaled according to a constant (0<fM≤1) to calculate the alveolar ventilation applied by the muscles. A value of fM<1 illustrates that the muscle cannot deliver the respiratory drive calculated by the chemical control model.

Part H of FIG. 6H, equation 14, describes the minute ventilation as alveolar ventilation plus ventilation of the dead space, that equal to the product of tidal volume (Vt) and respiratory frequency (f).

The model described above can be used to simulate respiratory control. The model enables simulation of the control of alveolar ventilation taking into account pulmonary gas exchange, blood and CSF acid-base status, circulation, tissue and interstitial buffering, and metabolism.

Figure 7:
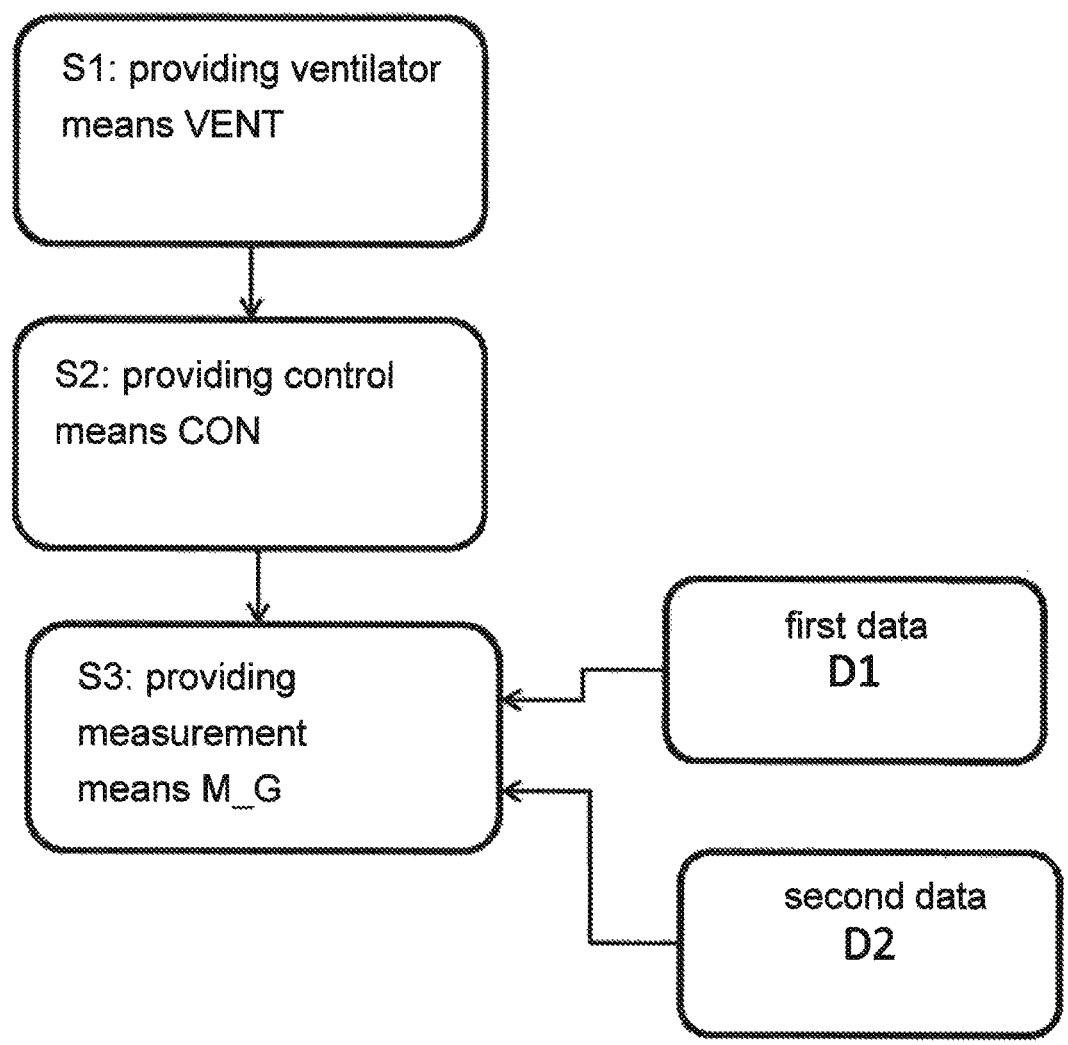
FIG. 7 is a schematic flow chart of a method according to the invention.

FIG. 7 is a schematic flow chart of a method according to the invention. The invention thus relates to a method for operating a mechanical ventilation system 10 for respiration aid of an associated patient 5, P, the method being adapted for estimating the respiratory drive R_drive of said patient, the method comprising:

S1 providing ventilator means VENT capable of mechanical ventilating said patient with air and/or one or more medical gases, S2 providing control means CON, the ventilator means being controllable by said control means by operational connection thereto, and S3 providing measurement means M_G arranged for measuring the respiratory feedback of said patient in the expired gas in response to the mechanical ventilation, the measurement means being capable of delivering first data D1 to said control means, wherein the control means is capable of operating the ventilation means by providing ventilatory assistance so that said patient is at least partly breathing spontaneously, and, when providing such ventilatory assistance, the control means being capable of changing one, or more, volume and/or pressure parameters Vt_SET of the ventilator means so as to detect changes in the respiratory feedback of said patient by the measurement means, the control means further being arranged for receiving second data (D2), preferably obtainable from blood analysis of said patient, said second data being indicative of the respiratory feedback in the blood of said patient, the control means being adapted for:
applying the first data D1 indicative of changes of respiratory feedback in expired air, and
applying the second data D2 indicative of the respiratory feedback in the blood, in a physiological model MOD capable of estimating one, or more, components, R_MUSC and/or R_CHEM, of the total respiratory drive, R_DRIVE, for the patient 5, P.

GLOSSARY

CSF Cerebral spinal fluid
Vt Respiratory volume in a single breath, tidal volume
Vt_SET Respiratory volume settings for mechanical ventilation, tidal volume
$FECO_2$ Fraction of carbon dioxide in expired gas.
$FE'CO_2$ Fraction of carbon dioxide in expired gas at the end of expiration.
$PECO_2$ Partial pressure of carbon dioxide in expired gas.
$PE'CO_2$ Partial pressure of carbon dioxide in expired gas at the end of expiration.

RR respiratory frequency (RR) or, equivalently, duration of breath (including duration of inspiratory or expiratory phase)
pHa Arterial blood pH
PaCO2 Pressure of carbon dioxide level,
SaO2 Oxygen saturation of arterial blood
PpO2 Pressure of oxygen in arterial blood In short, the present invention relates to a system 10 and a corresponding method for estimating the respiratory drive, R_DRIVE, of mechanically ventilated patients, and for preferably apportioning this respiratory drive into one, or more, components related to the chemical drive—i.e. the drive due to the chemoreceptor response- and/or the muscular drive—i.e. the contraction of respiratory muscles, for example the diaphragm. The principle of the invention is that respiratory drive can be obtained from measuring the patient's response to small changes in mechanical ventilation settings, Vt_SET, and that this can be apportioned into chemical and/or muscular effects depending upon the changes in respiratory frequency, and/or arterial or end tidal $CO_2$ levels, and/or arterial blood pH, as indicated in FIG. 1.

REFERENCES

1. The Acute Respiratory Distress Syndrome (ARDS) Network (2000) Ventilation with lower tidal volumes as compared with traditional tidal volumes for acute lung injury and the acute respiratory distress syndrome. N Engl. J Med. 342:1301-1308.
2. L. Brochard and A. W. Thille, "What is the proper approach to liberatng the weak from mechanical ventilation?," Critical Care, vol. 37, pp. 5410-5415, 2009.
3. Duffin, J. "The role of the central chemoreceptors: A modeling perspective." Respiratory Physiology and Neurobiology 173 (2010): 230-243.
   This reference is particularly relevant for the models on acid-base status of CSF (C), and respiratory drive (F) as shown in FIG. 6.
4. Duffin, J. "Role of acid-base balance in the chemoreflex control of breathing." J Appl Physiol 99 (2005): 2255-2265.
   This reference is also particularly relevant for the models on acid-base status of CSF (C) and respiratory drive (F) as shown in FIG. 6.
5. S. E. Rees, C. Allerød, D. Murley, Y. Zhao, B. W. Smith, S. Kjaergaad, P. Thorgaad and S. Andreassen, "Using physiological models and decision theory for selecting appropriate ventilator settings," Journal of Clinical Monitoring and Computing, vol. 20, pp. 421-429, 2006.
6. S. E. Rees, "The Intelligent Ventilator (INVENT) project: The role of mathematical models in translating physiological knowledge into clinical practice," Computer Methods and Programs in Biomedicine, vol. 104S, pp. S1-S29, 2011.
   This reference is particularly relevant for the models of pulmonary gas exchange (A); acid-base status and oxygenation of blood (B); circulation and blood in arterial and mixed venous pools (D); interstitial fluid and tissue buffering, and metabolism (E), as shown in FIG. 6.

All patent and non-patent references cited in the present application, are hereby incorporated by reference in their entirety.

ANNEX WITH EMBODIMENTS

In a separate aspect, the invention relates to the following embodiments found in the priority founding Danish patent application PA 2013 70283:

1. A mechanical ventilation system (10) for respiration aid of an associated patient (5, P), the system being adapted for estimating the respiratory drive (R_drive) of said patient, the system comprising:
   ventilator means (11, VENT) capable of mechanical ventilating said patient with air and/or one or more medical gases,
   control means (12, CON), the ventilator means being controllable by said control means by operational connection thereto, and
   measurement means (11a, M_G) arranged for measuring the respiratory feedback of said patient in the expired gas (6) in response to the mechanical ventilation, the measurement means being capable of delivering first data (D1) to said control means,
   wherein the control means is capable of operating the ventilation means by providing ventilatory assistance so that said patient is at least partly breathing spontaneously, and, when providing such ventilatory assistance, the control means being capable of changing one, or more, volume and/or pressure parameters (Vt_SET) of the ventilator means so as to detect changes in the respiratory feedback of said patient by the measurement means,
   the control means further being arranged for receiving second data (D2), preferably obtainable from blood analysis of said patient, said second data being indicative of the respiratory feedback in the blood of said patient,
   the control means being adapted for using:
     the first data (D1) indicative of changes of respiratory feedback in expired air (6), and
     the second data (D2) indicative of the respiratory feedback in the blood (7),
   in a physiological model (MOD) capable of estimating the total respiratory drive (R_DRIVE) for the patient.
2. The mechanical ventilation system according to embodiment 1, wherein the physiological model (MOD) comprises a component of the total respiratory drive being indicative of muscular response (R_MUSC).
3. The mechanical ventilation system according to embodiment 1 or 2, wherein the physiological model (MOD) comprises a component of the total respiratory drive being indicative of chemical response (R_CHEM), preferably a subcomponent indicative of the central chemical response and a subcomponent indicative of the peripheral chemical response.
4. The mechanical ventilation system according to any of embodiments 1-3, wherein the control means is arranged for estimating both the muscular response (R_MUS) and chemical response (R_CHEM) forming part of the total respiratory drive (R_DRIVE).
5. The mechanical ventilation system according to any of embodiments 1-4, wherein the control means is arranged for estimating the muscular response (R_MUS) and chemical response (R_CHEM) by initially assuming one of the two responses; muscular response (R_MUS) or chemical response (R_CHEM), being a certain approximately constant level, preferably a normal level for said patient, and then subsequently iteratively solving for the other response.
6. The mechanical ventilation system according to embodiment 1, wherein the second data (D2) used in the physiological model (MOD) is indicative for oxygenation and/or acid-base status of the blood, preferably being related to the influence of the acid-base status on the cerebrospinal fluid (CSF).
7. The mechanical ventilation system according to embodiment 1, wherein the second data (D2) used in the physiological model (MOD) is indicative for the metabolism of said patient, preferably the tissue production of carbon dioxide ($CO_2$).

8. The mechanical ventilation system according to any of embodiment 1-7, wherein the physiological model (MOD) capable of estimating the total respiratory drive (R_DRIVE) for the patient is operationally connected to a medical decision support system (DSS), preferably for application in mechanical ventilation.

9. The mechanical ventilation system according to embodiment 1, wherein the measurement means (M_G) is arranged for measuring one or more of the following parameters consisting of: respiratory frequency (RR) or, equivalently, duration of breath (including duration of inspiratory or expiratory phase), and expiratory carbon dioxide levels ($FECO_2$), fraction of carbon dioxide in expired gas at the end of expiration, ($FE'CO_2$), partial pressure of carbon dioxide in expired gas ($PECO_2$), partial pressure of carbon dioxide in expired gas at the end of expiration ($PE'CO_2$), or equivalents thereof and/or combinations thereof.

10. The mechanical ventilation system according to 1, wherein the second data (D2), which is preferably obtainable from blood analysis (M_B) of said patient (P), is one or more parameters consisting of: arterial blood pH (pHa), pressure of carbon dioxide level (PaCO2), optionally measured transcutaneously (PtcC02), oxygen saturation of arterial blood (SaO2), pressure of oxygen in arterial blood (PpO2), or equivalents thereof and/or combinations thereof.

11. The mechanical ventilation system according to embodiment 1, wherein the respiratory drive is estimated without using a measurement of the electrical activity of the diaphragm of the patient.

12. The mechanical ventilation system according to embodiment 1, wherein the control means (CON) is capable of changing the level from one value to another value in one, or more, volume and/or pressure parameters of the ventilator means (Vt_SET) so as to detect the subsequent changes in the respiratory feedback of said patient by the measurement means.

13. The mechanical ventilation system according to embodiment 1, wherein the control means is capable of performing a change in one, or more, volume and/or pressure parameters of the ventilator means (Vt_SET) so as to detect associated changes in the respiratory feedback of said patient by the measurement means while performing said change.

14. The mechanical ventilation system according to embodiment 1, wherein the control means is capable of changing one, or more, volume and/or pressure parameters of the ventilator means by changing the inspiratory volume (Vt_SET) and/or the inspiratory pressure set by the ventilator means.

15. A method for operating a mechanical ventilation system for respiration aid of an associated patient, the method being adapted for estimating the respiratory drive (R_drive) of said patient, the method comprising:
   providing ventilator means (VENT) capable of mechanical ventilating said patient with air and/or one or more medical gases,
   providing control means (CON), the ventilator means being controllable by said control means by operational connection thereto, and
   providing measurement means (M_G) arranged for measuring the respiratory feedback of said patient in the expired gas in response to the mechanical ventilation, the measurement means being capable of delivering first data (D1) to said control means,
   wherein the control means is capable of operating the ventilation means by providing ventilatory assistance so that said patient is at least partly breathing spontaneously, and, when providing such ventilatory assistance, the control means being capable of changing one, or more, volume and/or pressure parameters (Vt_SET) of the ventilator means so as to detect changes in the respiratory feedback of said patient by the measurement means,
   the control means further being arranged for receiving second data (D2), preferably obtainable from blood analysis of said patient, said second data being indicative of the respiratory feedback in the blood of said patient,
   the control means being adapted for:
      applying the first data (D1) indicative of changes of respiratory feedback in expired air, and
      applying the second data (D2) indicative of the respiratory feedback in the blood,
   in a physiological model (MOD) capable of estimating the total respiratory drive (R_DRIVE) for the patient.

16. A computer program product being adapted to enable a computer system comprising at least one computer having data storage means in connection therewith to control a ventilation system (10) according to embodiment 15.

The invention claimed is:

1. A mechanical ventilation system for respiration aid of an associated patient, the system comprising:
   a ventilator configured for mechanical ventilation of said patient with air and/or one or more medical gases,
   a controller that is operably connected to said ventilator, and
   a detector configured to measure respiratory feedback of said patient in an expired air in response to the mechanical ventilation, the detector configured for delivering first data to said controller, the first data being indicative of changes of the respiratory feedback from the expired air,
   wherein the controller is configured for operating the ventilator by providing ventilatory assistance so that said patient is at least partly breathing spontaneously, and, when providing such ventilatory assistance, the controller is configured for changing volume and/or pressure parameters of the ventilator so as to detect changes in the respiratory feedback of said patient by the detector,
   the controller further being arranged for receiving the first data from the detector and second data, from a blood analysis of said patient, using a blood measurement unit, said second data being indicative of respiratory feedback from the blood of said patient,
   the controller being configured for estimating, by separating, at least two components of a respiratory drive of the patient by using the first data and the second data in a physiological model,
   wherein the respiratory drive is the patient's own capability to control respiration, the respiratory drive being a total respiratory drive controlled by a signaling from a brain to respiratory muscles and a response of the respiratory muscles to the signaling,
   wherein a first component of the at least two components of the total respiratory drive is a chemical response which is a component indicative of a signaling from the brain to the respiratory muscles and wherein a second component of the at least two components of the total respiratory drive is a muscular response which is a component indicative of a response of the respiratory muscles, the controller being further configured to simulate an expected respiratory feedback including respiratory frequency, arterial pH and end tidal carbon dioxide at different levels of volume or pressure support based on the physiological model for a first scenario a) when a muscle strength of the patient is normal, and a second scenario b) when the muscle strength cannot respond adequately to the different levels of volume or pressure support;

the controller being further configured for identifying the first component, or the second component, or both, as a cause for a deviation of the respiratory feedback detected by the detector from the expected respiratory feedback simulated by the controller;

the controller being further configured for apportioning the first and second components of the at least two components of the total respiratory drive by analyzing simulations of the first and second scenarios; and the mechanical ventilation system being further configured to output and display the at least two components of the total respiratory drive on a human-machine interface.

2. The mechanical ventilation system according to claim 1, further comprising an additional detector configured to measure an indication of muscular response.

3. The mechanical ventilation system according to claim 1, wherein the controller is configured to estimate the muscular response and the chemical response by initially assuming one of the muscular response and the chemical response being a certain approximately constant level, or a normal level for said patient, and then subsequently iteratively solving for whichever of the muscular response or the chemical response was not assumed to be of the certain approximately constant level.

4. The mechanical ventilation system according to claim 1, wherein the muscular response is initially assumed constant, or at a normal level for said patient, and the chemical response is estimated, the estimated chemical response being subsequently applied for modelling a respiratory feedback to be compared with a measured respiratory feedback of the patient, a deviation therebetween being a measure for an inadequate response capability of the patient.

5. The mechanical ventilation system according to claim 1, wherein the second data used in the physiological model is indicative for oxygenation and/or acid-base status of the blood, or is related to an influence of the acid-base status on the cerebrospinal fluid.

6. The mechanical ventilation system according to claim 1, wherein the second data used in the physiological model is indicative for a metabolism of said patient, or a tissue production of carbon dioxide.

7. The mechanical ventilation system according to claim 1, wherein the physiological model capable of estimating the at least two components of the total respiratory drive for the patient is operationally connected to a medical decision support system (DSS), for use in connection with the mechanical ventilation of the patient.

8. The mechanical ventilation system according to claim 1, wherein the detector is configured to measure one or more of the following parameters: respiratory frequency, duration of breath, expiratory carbon dioxide levels, fraction of carbon dioxide in expired gas at an end of expiration, partial pressure of carbon dioxide in the expired air, or partial pressure of carbon dioxide in the expired air at the end of expiration, and/or combinations thereof.

9. The mechanical ventilation system according to claim 8, wherein the duration of breath includes duration of inspiratory or expiratory phase.

10. The mechanical ventilation system according to 1, wherein the second data, which is from the blood analysis of said patient, comprises one or more parameters of: arterial blood pH, pressure of carbon dioxide level, transcutaneously measured pressure of carbon dioxide, oxygen saturation of arterial blood, or pressure of oxygen in arterial blood, and/or combinations thereof.

11. The mechanical ventilation system according to claim 1, wherein the respiratory drive is estimated without using a measurement of the electrical activity of the diaphragm of the patient.

12. The mechanical ventilation system according to claim 1, wherein the controller is configured to change a level from one value to another value in volume and/or pressure parameters of the ventilator so as to detect subsequent changes in the respiratory feedback of said patient by the detector.

13. The mechanical ventilation system according to claim 1, wherein the controller is capable of changing volume and/or pressure parameters of the ventilator by changing an inspiratory volume and/or an inspiratory pressure set by the ventilator.

14. The mechanical ventilation system according to claim 1, further comprising a computer program product being adapted to enable a computer system comprising at least one computer having data storage in connection therewith to control the mechanical ventilation system.

15. The mechanical ventilation system according to claim 1, wherein identification of the cause for the deviation and apportionment of the first component and the second component comprise:

for the first scenario, assuming that the chemical response is also at a normal level for said patient, a first curve is calculated representing simulation of the expected respiratory feedback including the respiratory frequency, arterial pH and end tidal carbon dioxide at different levels of volume or pressure support, for the first scenario, assuming that the chemical response is adapted to said patient, thereby providing an adaptation to chemical response, a second curve is calculated representing simulation of the expected respiratory feedback including the respiratory frequency, arterial pH and end tidal carbon dioxide at different levels of volume or pressure support, the adaptation to chemical response including inputting the first data and the second data into the physiological model for said patient, a deviation of the second curve from the first curve represents a change of the chemical response from the normal level of said patient, and a deviation of the second curve from the respiratory feedback measured from said patient represents a reduced muscle response.

16. The mechanical ventilation system according to claim 1, wherein identification of the cause for the deviation and apportionment of the first component and the second component comprise:

for the first scenario, assuming that the chemical response is at a normal level for said patient, a first curve is calculated representing simulation of the expected respiratory feedback including the respiratory frequency, arterial pH and end tidal carbon dioxide at different levels of volume or pressure support, for the first scenario, assuming that the chemical response is adapted to said patient, thereby providing an adaptation to chemical response, a second curve is calculated representing simulation of the expected respiratory feedback including the respiratory frequency, arterial pH and end tidal carbon dioxide at different levels of volume or pressure support, the adaptation to chemical response including inputting the first data and the second data into the physiological model for said patient, for the second scenario, assuming that the chemical response is adapted to said patient, a third curve is calculated representing simulation of the expected respiratory feedback including the respiratory frequency, arterial pH and end tidal carbon dioxide, the adaptation to chemical response including inputting the first data and the second data into the physiological model for said patient, wherein an adaptation to muscular response is quantified by a weighting factor, a deviation of the second curve from the first curve represents a change of the chemical response from the normal level of said patient, a deviation of the third curve from the second curve represents a reduced muscle response, a deviation of the third curve from the first curve represents both the change of the chemical response from the normal level of said patient and the reduced muscle response wherein the apportionment of the two components of the respiratory drive is based on analysis of each of the deviations and the weighting factor.

17. A method for operating a mechanical ventilation system for respiration aid of an associated patient, the method comprising:

providing a ventilator configured for mechanically ventilating said patient with air and/or one or more medical gases, providing a controller, the ventilator being controllable by said controller by operational connection thereto, providing a detector configured to measure respiratory feedback of said patient in an expired air in response to the mechanical ventilation, the detector being configured for delivering first data to said controller, the first data being indicative of changes of the respiratory feedback from the expired air, and providing a human-machine interface for displaying output results, wherein the controller is configured for operating the ventilator by providing ventilator assistance so that said patient is at least partly breathing spontaneously, and, when providing such ventilatory assistance, the controller is configured for changing one, or more, volume and/or pressure parameters of the ventilator so as to detect changes in the respiratory feedback of said patient by the detector, the controller further being arranged for receiving the first data from the detector and second data, from a blood analysis of said patient, using a blood measurement unit, said second data being indicative of respiratory feedback from the blood of said patient, the controller being configured for estimating, by separating, at least two components of a respiratory drive of the patient by using the first data and the second data in a physiological model, wherein the respiratory drive is the patient's own capability to control respiration, the respiratory drive being a total respiratory drive controlled by a signaling from a brain to respiratory muscles and a response of the respiratory muscles to the signaling, wherein a first component of the at least two components of the total respiratory drive is a component indicative of a chemical response which is a signaling from the brain to the respiratory muscles and wherein a second component of the at least two components of the total respiratory drive is a muscular response which is a component indicative of a response of the respiratory muscles, simulating by the controller an expected respiratory feedback including respiratory frequency, arterial pH and end tidal carbon dioxide at different levels of volume or pressure support based on the physiological model for a first scenario a) when a muscle strength of the patient is normal, and a second scenario b) when the muscle strength cannot respond adequately to the different levels of volume or pressure support;

identifying by the controller the first component, or the second component, or both, as a cause for a deviation of the respiratory feedback detected by the detector from the respiratory feedback simulated by the controller;

by analyzing simulations of the first and second scenarios, apportioning the first and second components of the at least two components of the total respiratory drive; and outputting the total respiratory drive and the at least two components of the total respiratory drive to the human-machine interface.

18. The method according to claim 17, wherein the identifying and apportioning comprise:

for the first scenario, assuming that the chemical response is also at a normal level for said patient, calculating a first curve representing simulation of the expected respiratory feedback including the respiratory frequency, arterial pH and end tidal carbon dioxide at different levels of volume or pressure support, for the first scenario, assuming that the chemical response is adapted to said patient, thereby providing an adaptation to chemical response, calculating a second curve representing simulation of the expected respiratory feedback including the respiratory frequency, arterial pH and end tidal carbon dioxide at different levels of volume or pressure support, the adaptation to chemical response including inputting the first data and the second data into the physiological model for said patient, identifying a change of the chemical response from the normal level of said patient as a cause for a deviation of the second curve from the first curve for said patient, and identifying a reduced muscle response as a cause for a deviation of the second curve from the respiratory feedback measured from said patient.

19. The method according to claim 17, wherein the identifying and apportioning comprise:

for the first scenario, assuming that the chemical response is at a normal level for said patient, calculating a first curve representing simulation of the expected respiratory feedback including the respiratory frequency, arterial pH and end tidal carbon dioxide at different levels of volume or pressure support, for the first scenario, assuming that the chemical response is adapted to said patient, thereby providing an adaptation to chemical response, a second curve representing simulation of the expected respiratory feedback including the respiratory frequency, arterial pH and end tidal carbon dioxide at different levels of volume or pressure support, the adaptation to chemical response including inputting the first data and the second data into the physiological model for said patient, for the second scenario, assuming that the chemical response is adapted to said patient, a third curve is calculated representing simulation of the expected respiratory feedback including the respiratory frequency, arterial pH and end tidal carbon dioxide, the adaptation to chemical response including inputting the first data and the second data into the physiological model for said patient, wherein an adaptation to muscular response is quantified by a weighting factor, identifying a change of the chemical response from the normal level of said patient as a cause for a deviation of the second curve from the first curve, identifying a reduced muscle response as a cause for a deviation of the third curve from the second curve, identifying both the change of the chemical response from the normal level of said patient and the reduced muscle response as a cause for a deviation of the third curve from the first curve and apportioning the two components of the respiratory drive based on the previous identifying steps and the weighting factor.

20. A mechanical ventilation system for respiration aid of an associated patient, the system comprising:

a ventilator configured for mechanical ventilation of said patient with air and/or one or more medical gases, a controller that is operably connected to said ventilator, a detector configured to measure respiratory feedback of said patient in an expired air in response to the mechanical ventilation, the detector configured for delivering first data to said controller, the first data being indicative of changes of the respiratory feedback from the expired air, and a human-machine interface configured for displaying output results, wherein the controller is configured for operating the ventilator by providing ventilatory assistance so that said patient is at least partly breathing spontaneously, and, when providing such ventilatory assistance, the controller is configured for changing volume and/or pressure parameters of the ventilator so as to detect changes in the respiratory feedback of said patient by the detector, the controller further being arranged for receiving the first data from the detector and second data, from a blood analysis of said patient, using a blood measurement unit, said second data being indicative of respiratory feedback from the blood of said patient, the controller being configured for estimating, by separating, at least two components of a respiratory drive of the patient by using the first data and the second data in a physiological model, wherein the respiratory drive is the patient's own capability to control respiration, the respiratory drive being a total respiratory drive controlled by a signaling from a brain to respiratory muscles and a response of the respiratory muscles to the signaling, wherein a first component of the at least two components of the total respiratory drive is a component indicative of a chemical response which is a signaling from the brain to the respiratory muscles and wherein a second component of the at least two components of the total respiratory drive is a muscular response which is a component indicative of a response of the respiratory muscles, wherein the total respiratory drive and the at least two components of the total respiratory drive are outputted to and displayed on the human-machine interface, the controller being further configured to simulate an expected respiratory feedback including respiratory frequency, arterial pH and end tidal carbon dioxide at different levels of volume or pressure support based on the physiological model for a first scenario a) when a muscle strength of the patient is normal, and a second scenario b) when the muscle strength cannot respond adequately to the different levels of volume or pressure support;

the controller being further configured for identifying the first component, or the second component, or both, as a cause for a deviation of the respiratory feedback detected by the detector from the expected respiratory feedback simulated by the controller;

the controller being further configured for apportioning the first and second components of the at least two components of the total respiratory drive by analyzing simulations of the first and second scenarios; and the at least two components of the total respiratory drive outputted to and displayed on the human-machine interface allowing a clinician to configure the ventilator based on the at least two components.

* * * * *